(12) United States Patent
Tschirren et al.

(10) Patent No.: US 10,894,127 B2
(45) Date of Patent: Jan. 19, 2021

(54) SAFETY MECHANISM FOR AN AUTOINJECTOR

(71) Applicant: Ypsomed AG, Burgdorf (CH)

(72) Inventors: Markus Tschirren, Burgdorf (CH); Juerg Hirschel, Bern (CH)

(73) Assignee: Ypsomed AG, Burgdorf (CH)

( * ) Notice: Subject to any disclaimer, the term of this patent is extended or adjusted under 35 U.S.C. 154(b) by 392 days.

(21) Appl. No.: 15/217,532

(22) Filed: Jul. 22, 2016

(65) Prior Publication Data

US 2016/0325044 A1 Nov. 10, 2016

Related U.S. Application Data

(63) Continuation of application No. PCT/CH2015/000004, filed on Jan. 21, 2015.

(30) Foreign Application Priority Data

Jan. 30, 2014 (EP) .................................... 14153335

(51) Int. Cl.
*A61M 5/20* (2006.01)
*A61M 5/32* (2006.01)

(52) U.S. Cl.
CPC ........ *A61M 5/2033* (2013.01); *A61M 5/3202* (2013.01); *A61M 5/3204* (2013.01);
(Continued)

(58) Field of Classification Search
CPC ........ A61M 5/3204; A61M 2005/2013; A61M 5/2033; A61M 5/3202; A61M 2005/206; A61M 2005/2073; A61M 2005/3215
See application file for complete search history.

(56) References Cited

U.S. PATENT DOCUMENTS

2004/0039336 A1 2/2004 Amark et al.
2007/0135767 A1* 6/2007 Gillespie, III ...... A61M 5/2033
                                                          604/135
(Continued)

FOREIGN PATENT DOCUMENTS

EP    2742962 A2    6/2014
GB    2 467 904 A   8/2010
(Continued)

OTHER PUBLICATIONS

International Search Report dated Feb. 20, 2015 for PCT/CH2015/000004 filed Jan. 21, 2015.
(Continued)

*Primary Examiner* — Scott J Medway
(74) *Attorney, Agent, or Firm* — Dorsey & Whitney LLP (57) ABSTRACT

An autoinjector for dispensing a fluid product, in particular a medicament, comprises: a) a housing (2) and a product container (13), in particular a syringe, arranged in the housing and has a piston displaceable in a distal direction, by means of an advancement member, in order to dispense the product contained in the product container, b) a removable covering cap (4) arranged at the distal end of the housing, c) a triggering member (3), which, in the starting position, projects beyond the distal end of the housing, d) where the triggering member, in order to trigger the dispensing operation, can move in a proximal direction relative to the housing from the starting position into a triggering position when the covering cap has been removed from the housing, and e) where the triggering member is blocked against movement into the triggering position when the covering cap is arranged on the housing.

19 Claims, 4 Drawing Sheets

(52) U.S. Cl.
CPC ............... *A61M 2005/2013* (2013.01); *A61M 2005/2073* (2013.01)

(56) References Cited

U.S. PATENT DOCUMENTS

| | | | |
|---|---|---|---|
| 2012/0053528 A1* | 3/2012 | Bollenbach | A61M 5/24 604/192 |
| 2012/0203186 A1* | 8/2012 | Vogt | A61M 5/2033 604/192 |
| 2013/0018313 A1 | 1/2013 | Kramer et al. | |

FOREIGN PATENT DOCUMENTS

| | | |
|---|---|---|
| WO | WO 1994/011041 | 5/1994 |
| WO | WO 2008/113199 | 9/2008 |
| WO | WO 2008/113864 | 9/2008 |
| WO | WO 2009/114542 | 9/2009 |
| WO | WO 2009/155277 | 12/2009 |
| WO | WO 2010/136078 | 12/2010 |
| WO | WO 2011/012849 | 2/2011 |
| WO | 2014009705 A1 | 1/2014 |

OTHER PUBLICATIONS

International Preliminary Report on Patentability dated Aug. 2, 2016 PCT/CH2015/000004 filed Jan. 21, 2015.

* cited by examiner

SAFETY MECHANISM FOR AN AUTOINJECTOR

CROSS-REFERENCE TO RELATED APPLICATIONS

This application is a Continuation of International Patent Application No. PCT/CH2015/000004 filed Jan. 21, 2015, which claims priority to European Patent Application No. 14153335.6 filed Jan. 30, 2014, the entire contents of each are incorporated herein by reference for any and all purposes.

BACKGROUND

The invention relates to a safety mechanism for an autoinjector for preventing unwanted dispensing of product. The autoinjector is used for dispensing a fluid product, in particular, a medication.

An autoinjector is an injection device by means of which a fluid product contained in a product container can be dispensed by a drive mechanism such as a prestressed spring or a gas generator, for example, and administered to a patient.

Autoinjectors are known in the prior art. For example, in European Patent Application No. 13 178 676.6, an autoinjector is described, which comprises a syringe fixed in the housing. For the administration, a needle guard sleeve used as triggering member is set on the desired puncture site of the patient. As a result of the autoinjector being pressed against the puncture site, the needle guard sleeve is backed into the housing, wherein, on the one hand, the needle of the syringe is stuck into the patient, and, on the other hand, the drive mechanism is activated, as a result of which the product contained in the product container is expelled by a forward drive member through the needle.

From WO 2008/113199 A1, an autoinjector is known, in which the needle guard sleeve is also set on the desired puncture site, and backed into the housing by pressing of the autoinjector on the puncture site. As a result, a puncturing sequence is triggered, by means of which the product container is shifted relative to the housing in the distal direction until the needle protrudes beyond the distal end of the needle guard sleeve and is stuck into the patient. At the end of the puncturing sequence, a dispensing sequence is triggered, in which a forward drive member expels the product contained in the product container through the needle and injects it into the patient. At the end of the injection, the autoinjector is removed from the puncture site, as a result of which a retraction sequence is initiated, by means of which the product container is shifted relative to the housing in the proximal direction, as a result of which the needle is retracted into the distal end of the autoinjector, in order to prevent injuries.

In addition, autoinjectors exist that are triggered as in the above-mentioned prior art, i.e., by shifting of a needle guard sleeve into the housing, wherein the product container can be shifted relative to the housing only for the purpose of the puncturing, wherein the needle remains in the protruding position after the puncturing. For the protection of the needle, the needle guard sleeve is shifted over the distal end of the needle, and, in particular, locked, in order to prevent a renewed backing of the needle guard sleeve into the housing.

As a result of the design consisting in triggering the puncturing or dispensing by the backing movement of the triggering member, which is often a needle guard sleeve, into the housing, there is a risk that the dispensing of product can be triggered accidentally, for example, if the autoinjector is dropped or otherwise strongly jolted. In the process, the triggering member can be shifted by its own inertia relative to the housing into its triggering position, as a result of which the dispensing of product is triggered unintentionally.

WO 2009/114542 A1 proposes a safety mechanism that is attached at the end opposite that of the needle, i.e., at the proximal end, and has to be removed before the triggering of the autoinjector. The safety mechanism blocks the movement of the trigger sleeve into its triggering position. In order to prepare the autoinjector for dispensing, a covering cap arranged at the distal end of the autoinjector is removed, and the safety mechanism attached at the proximal end is removed. As a result of the two steps that have to be carried out separately from one another for preparing the autoinjector, an intuitive operation is made more difficult.

Other autoinjectors are known from US 2004/0039336 A1 and WO 94/11041 A1.

SUMMARY

An object of the invention is to provide an autoinjector that prevents accidental triggering of the puncturing or dispensing sequence and that can be operated intuitively.

The object is attained by the autoinjector according to the present disclosure, including the claims, the description, and the figures.

The invention is based on an autoinjector for dispensing a fluid product, in particular a medication. The autoinjector comprises a housing that is preferably elongate and/or sleeve-like. The housing is used for being gripped with one hand by the user of the device. A product container is arranged in the housing. In particular, the product container can be a syringe comprising a syringe body at the distal end of which an injection needle is firmly arranged. The preferably cylindrical syringe body encloses a piston, which can be shifted relative to the syringe body and is shifted to the distal end for the dispensing of product, as a result of which the fluid product arranged between the piston and the injection needle, in particular a medication, is dispensed through the injection needle from the product container. At its proximal end, i.e. its rear end or opposite end from the injection needle, the syringe body can have a flange, which can also be referred to as a finger flange. A syringe of such design is available as standard syringe, so that it is not necessary to develop a specially adapted syringe for the autoinjector. The piston sealingly abuts against the inner diameter of the syringe body.

The preferably elongate, sleeve-like housing forms the longitudinal axis of the autoinjector. The housing is preferably cylindrical, in particular circular cylindrical. The product container is arranged in the housing. For example, the container can be arranged in a manner so that it can be shifted in the housing, i.e., it can be shifted relative to the housing in the distal direction for automatic puncturing, so that the needle tip protrudes from an opening at the distal end of the autoinjector and can be stuck automatically into the patient. In such a device, after a completion of product dispensing, the needle tip can be moved into the distal end of the device, in particular the product container can be moved relative to the housing in the proximal direction.

In preferred embodiments, the product container is held in a manner so that it cannot be shifted along the longitudinal axis in the housing, in particular by means of a product container holder or syringe holder that holds the product container in an axially fixed position and is connected in an axially fixed manner to the housing, in particular engaged therewith. The needle tip preferably protrudes distally beyond the distal end of the housing. As a result, the needle can be stuck into the puncture site by a movement of the housing towards the patient.

The autoinjector comprises, in particular, a sleeve-like triggering member, which protrudes in its starting position beyond the distal end of the housing. The triggering member is used primarily for triggering the dispensing of product or possibly the puncturing sequence. Optionally, the triggering member can be used as needle guard sleeve and can be referred to as such. The triggering member forming the distal end of the autoinjector can have an opening for the injection needle, wherein the injection needle can pass through the opening. The triggering member can be arranged in its starting position relative to the needle tip in such a manner that the triggering member, in particular the needle guard sleeve, protrudes distally beyond the needle tip or so that the needle tip protrudes distally beyond the distal end of the triggering member. The triggering member can be shifted relative to the housing by an actuation stroke from its starting position in the proximal direction into an actuated position, in particular actuation position, in particular it can be shifted into the housing, so that the needle projects or projects forward from the distal end or through the opening of the triggering member. Preferably, the triggering member can be shifted by a needle guard stroke from the starting position relative to the housing in the distal direction into a needle guard position, in which the distal end of the triggering member, in particular of the needle guard sleeve, protrudes distally beyond the needle tip, so as to reduce, after the use of the device or after dispensing of product, the risk of injury that would be associated with an exposed needle tip.

The triggering member can be shifted in the proximal direction, for example, against the force of a spring, which can be referred to as resetting spring or needle guard spring, wherein the spring can shift the triggering member in the distal direction from the position in which a barring means bars the movement of the triggering member in the proximal direction, or from the triggering position in the distal direction, for example, into the needle guard position.

The autoinjector can comprise, for example, a spring-mounted locking member, which locks the triggering member in its needle guard position, in particular with regard to the housing, and which blocks a backing movement of the triggering member in the proximal direction or into the housing. The locking member locks the triggering member at least so that the needle cannot protrude from the distal end of the triggering member. For example, the triggering member can be shifted from the needle guard position in the proximal direction only to the extent that the needle tip does not protrude from the distal end of the triggering member.

The autoinjector comprises a covering cap that is arranged at the distal end of the housing, particularly in the delivery state of the autoinjector. The covering cap can be removed from the housing, in particular it can be pulled off or twisted off, in particular unscrewed. For the preparation of the autoinjector for the intended use, the covering cap is removed from the housing. The covering cap is preferably attached on the housing, and it encloses the distal end of the triggering member, and, in particular, it prevents access to the distal end of the triggering member. When the covering cap has been removed from the housing, access to the triggering member is allowed, so that the latter can be set on the puncture site.

The triggering member, which is, in particular, sleeve-like, and which protrudes in its starting position beyond the distal end of the housing, can be moved, for the purpose of triggering the dispensing, relative to the housing from the starting position in a proximal direction into the triggering position, when the covering cap has been removed from the housing. The triggering member is coupled to a drive mechanism in such a manner that the drive mechanism allows the dispensing of product and/or possibly the puncturing sequence when the triggering member is in its triggering position or reaches the triggering position.

According to the invention, the triggering member is blocked against movement into the triggering position when the covering cap is arranged on the housing. For example, the triggering member may be moved not at all or only by a stroke in the distal direction that is less than the trigger stroke, i.e., the stroke that the triggering member performs during the movement from the starting position into the triggering position.

Preferably, the autoinjector can comprise a forward drive member, which, at least during the dispensing of product, acts on the piston, and which, in particular, abuts against the piston, and a dispensing spring that acts on the forward drive member, and which, for example, in particular, is braced on the forward drive member with its distal end. The forward drive member can be sleeve-like, for example, and form a shoulder, which is arranged, for example, in the area of the distal end of the forward drive member, and against which the distal end of the dispensing spring can be braced. The dispensing spring can be arranged preferably within the, for example, sleeve-like forward drive member. The dispensing spring is preferably formed as a coil spring, made of metal, for example, acting as compression spring. The dispensing spring can be prestressed sufficiently, in particular in the delivery state of the autoinjector, so that it or the energy stored in it is sufficient to dispense—essentially as above—the product from the product container by displacing the forward drive member by one dispensing stroke. As a result of the shifting of the forward drive member by the dispensing stroke, the piston is also shifted. If, in the delivery state, there is a gap between the piston and the forward drive member, the dispensing stroke of the piston is smaller than the dispensing stroke of the forward drive member, which is preferable, since the piston remains unstressed until use, as a result of which an unintended premature dispensing of product is avoided. However, in principle, it is also possible for the forward drive member to adjoin the piston in the delivery state and not only at the time of the dispensing of product. If, in the delivery state, the forward drive member already abuts against the piston, the dispensing stroke of the piston corresponds to the dispensing stroke of the forward drive member. The proximal end of the dispensing spring can be braced on the housing or on an element that is fixed on the housing, in particular also on an element that is only temporarily axially fixed relative to the housing.

It is particularly advantageous to use the invention with the autoinjector from European Patent Application No. 13 178 676.6 or WO 2008/113199 A1, wherein the content of these applications is included in this application by reference for any useful purpose.

The triggering member can comprise or form, for example, a barring means that is arranged by linkage or preferably spring mounted. The triggering member can comprise a sleeve-like main body on which the barring means is arranged by linkage or spring mounted, in particular forming a single piece with the main body. The barring means can be deflected by the covering cap into a barring position, in which the barring means faces a stop formed by the autoinjector, in particular in alignment with the stop. In its release position, which the barring means assumes when the cap is removed, the barring means can be moved past the stop, i.e., not in alignment with the stop. The covering cap can thus form an actuator, which presses or can move the barring means into the release position, in particular relative to the main body, when the covering cap is arranged on the housing. When the covering cap is removed from the housing, this actuator is missing, as a result of which the barring means is no longer pressed or can no longer be pressed in its barring position. When the covering cap is removed from the housing, this advantageously results in the user of the autoinjector at the same time unbarring the triggering member for movement from the starting position into the triggering position. When the covering cap is arranged on the housing, the triggering member is blocked or barred against movement into the triggering position. Due to the barring means, the autoinjector can no longer be triggered due to inertia of the triggering member in the case of strong vibration.

Advantageously, the barring means is arranged, in particular, so as to form a single piece with the triggering member or its main body, in such a manner that it springs into its release position when it is unloaded and it can be deflected out of its release position against its spring force.

Advantageously, the housing or an element that is fixed to the housing, such as the product container holder or syringe holder, forms the stop. The barring means formed by the triggering member is moved along with the triggering member during the movement along the longitudinal axis of the autoinjector, i.e., in particular it is also moved along during the movement of the triggering member in the proximal direction. In the process, the barring means abuts against the stop and thus prevents further movement of the triggering member in the proximal direction to the point at which it is in its triggering position.

The covering cap can comprise, for example, an actuator surface that presses the barring means into its barring position or retains it in its barring position. For example, the covering cap can have a retention surface against which the barring means abuts, when the latter is in its barring position. For example, the retention surface can be the actuator surface or a surface separate from the actuator surface.

In particular, the barring means, particularly a contact surface of the barring means, which can abut against the stop, can be at a distance from the stop along the longitudinal axis when the triggering member is in its starting position. As a result, although the triggering member is in principle allowed to be moved from its starting position in the proximal direction, it is not allowed to be moved as far as into its triggering position. This results, on the one hand, in that relatively large manufacturing tolerances are made possible, and, on the other hand, in that the barring means is prevented from becoming jammed on the stop and no longer moving into its release position, even when the covering cap has been removed.

The retention surface or the actuator surface can be configured so that it retains the barring means in the barring position when the triggering member or actuation element is in its starting position. The barring means can abut against and/or slide along the retention surface, for example, when the triggering member is shifted from the starting position in the proximal direction against the spring or its spring force, and/or it is shifted out of the position in which the barring means bars the movement of the triggering member in the proximal direction, by the spring or its spring force in the distal direction, for example, back into the starting position.

Alternatively, the retention surface can be configured so that the barring means, which can be moved together with the triggering element, comes in contact with the retention surface only when the barring means, in particular its contact surface, has been shifted towards the stop, and the triggering member has been shifted from the starting position in the proximal direction. In particular, in this alternative as well, the triggering member can be shifted from the starting position against the spring or its spring force in the proximal direction and/or from the position in which the barring means bars the movement of the triggering member in the proximal direction, by the spring or its spring force in the distal direction, for example, back into the starting position. In the starting position, the barring means can be in its release position or in a position different from the barring position even with covering cap mounted. This has the advantage that certain material-related disadvantages of plastic can be eliminated. Indeed, some plastics have the disadvantage that they tend to exhibit retardation or creep, i.e., plastic deformation under a load. Indeed, already in the starting position of the triggering member, if the barring means is deflected, in particular resiliently, out of its release position into its barring position, it can happen that, in the case of prolonged storage, but also particularly as a function of the temperature, a plastic deformation of the spring-mounted linkage of the barring means occurs, the result of which is that the barring means no longer springs back into its release position when the covering cap is removed from the housing. In this case, the triggering member would no longer be moved into its triggering position, in spite of the covering cap having been removed. This could also be the case if the triggering member were to remain in its position in which the barring means abuts against the stop. The spring can advantageously be moved in the proximal direction, for example, back into the starting position, so that the barring means is moved out of the barring position by the return movement of the triggering member.

In other words, it is preferable that the covering cap, in particular the actuator surface and/or the retention surface, deflect the barring means into its barring position only when the triggering element is moved from its starting position in the proximal direction. As a result, it is ensured that the barring means moves into the barring position only when, with covering cap mounted, the triggering member is moved from its starting position in the proximal direction, as, for example, in the case of a vibration possibly generated by dropping the autoinjector on the floor, for example.

For example, the barring means can be moved by the actuator surface into the barring position and subsequently held by the retention surface in the barring position and/or slide along the retention surface when the triggering member is moved against the spring or its spring force from the starting position into the position in which the barring member abuts against the stop. In particular, the barring means can be retained by the retention surface in the barring position and/or slide along the retention surface and subsequently slide along the actuator surface, and in the process, spring out of the barring position when the triggering member is moved by the spring or its spring force from its position in which the barring member abuts against the stop, in the distal direction, in particular into the starting position.

The barring means can preferably have a contact surface facing in the proximal direction, which abuts against the stop when the triggering member is moved from its starting position in proximal direction and the barring means is in its barring position. The contact surface can be formed, for example, by the free end of the preferably arm- or tongue-shaped barring means, wherein the barring means is connected, for example, via the spring-mounted linkage in a manner so as to form a single piece with the triggering member or its main body.

The barring means can comprise, for example, a cam that protrudes, for example, from the arm- or tongue-shaped barring means towards the longitudinal axis, for example. The barring means can abut against the retention surface and/or it can slide on the covering cap or the retention surface or the actuator surface, as a result of which the cam and hence the barring means are deflected by the covering cap. For example, the cam can be deflected by the retention surface or the actuator surface, in particular when the triggering member is moved in the proximal direction.

In particularly preferable embodiments, the triggering member can comprise a sleeve-like section, which can be formed by the main body, for example, wherein a first slot is formed between the sleeve-like section and the barring means. Advantageously, the sleeve-like section surrounds the barring means. The housing can comprise another sleeve-like section, wherein a second slot is formed between the sleeve-like section of the housing and the stop. For example, the sleeve-like section of the housing can surround the stop. It is preferable that the sleeve-like section of the triggering member be moved into the second slot and/or the stop be moved into the first slot when the triggering member is moved from the starting position into the triggering position. As a result, it is possible to achieve, for example, a particularly space-saving arrangement for one of the known autoinjectors, without requiring more extensive changes in construction.

Particularly preferably, the needle can be covered with a needle covering cap, which can optionally be referred to as needle guard cap, and which is attached to the product container. The product container can have an area, for example distally relative to the cylindrical section, which encloses the needle, and which is firmly connected to the needle and the cylindrical section of the product container. The needle covering cap can be attached in this area. In general, the needle can be attached by frictional locking and/or positive locking to the product container, in particular to the area. The needle covering cap can be, for example, a cap made of a resilient material such as a rubber, for example. Alternatively, the needle covering cap can be formed by a rigid, for example, sleeve-like material, wherein such covering caps are known as "rigid needle shield." The covering cap is coupled, in particular, to the needle covering cap that is separate therefrom in such a manner that the needle covering cap is removed from the product container when the covering cap is removed from the housing. For this purpose, the covering cap can comprise an engagement member that engages on or in the needle covering cap, so that the needle covering cap is pulled off at the same time. For example, the engagement member can be a claw that clings to the needle covering cap. Alternatively, the engagement member can be a hook-like element, which engages, for example, on the proximal end of the needle covering cap, in particular which engages in the slot between the needle covering cap and the shoulder where the cylindrical area of the syringe body tapers. When the covering cap is removed, the hook-like engagement member then pulls the needle covering cap off the product container or injection needle.

DETAILED DESCRIPTION

The autoinjector comprises a sleeve-like, elongate housing 2 with a longitudinal axis L. In FIGS. 1a to 4b, only the front or distal section of the autoinjector is represented. The drive mechanism accommodated in the distal or rear portion is familiar to the competent person skilled in the art and can be designed, for example, as in European Patent Application No. 13 178 676.6 or as in WO 2008/113199 A1 previously incorporated by reference.

At the distal end of the autoinjector, in its delivery state (FIGS. 1b and 1b), a covering cap 4 is arranged, which is attached to the housing 2, for example, by frictional locking and/or positive locking, and which is pulled or screwed off and removed before the use of the autoinjector.

In the housing 2, a product container 13 in the form of a syringe is accommodated in a manner so that it can or cannot be shifted along the longitudinal axis L, for example, relative to the housing 2. The product container 13 has a sleeve-like syringe body, which encloses a piston that sealingly abuts against the inner periphery of the syringe body. At its distal end, the syringe body has an injection needle 13a that is connected, in particular, non-detachably to the syringe body, the distal end of said injection needle being formed by the needle tip. Between the injection needle 13a and the piston 3, a liquid product, in particular a medication, is arranged inside the syringe body, wherein the liquid product is dispensed from the product container 13 through the hollow injection needle 13a, by shifting the piston in a dispensing direction, i.e., in the distal direction or towards the injection needle 13a. At its proximal end, the syringe body has a so-called finger flange (not shown), which protrudes radially outward beyond the outer periphery of the cylindrical syringe body.

The product container 13 is accommodated in a product container holder, referred to as syringe holder 1, so that it is secured at least against a movement along the longitudinal axis L in distal direction relative to the syringe holder 1. The syringe holder 1 can be connected by positive locking to the housing 2, in particular by engagement therewith, or it can be shiftable relative to the housing along the longitudinal axis L, depending on the design of the autoinjector. If the syringe holder 1 is engaged with housing 2, the housing 2 can have recesses for this purpose, in which locking elements formed on the syringe holder 1 engage. The syringe holder 1 has at least one shoulder that protrudes inward, on which a tapering section of the product container 13, which is arranged distally relative to the cylindrical syringe body, is braced.

At its distal end, the autoinjector comprises a sleeve-like triggering member 3, in particular a needle guard sleeve, which, in its starting position (e.g., FIGS. 1a, 1b, 3a and 3b) protrudes beyond the distal end of the housing 2. With covering cap 4 mounted, the triggering member 3 is completely enclosed by said covering cap. The triggering member 3 has a spring-mounted barring means 31, which is designed in the shape of a tongue or arm. The elongate barring means 31 extends approximately parallel to the longitudinal axis L and faces with its free end in the proximal direction. With its other end, it is connected so as to form a single piece via a spring-mounted section to the triggering member 3, in particular to a sleeve-like main body of the triggering member 3, in particular with its distal end. The free end forms a contact surface 32 for a stop 21 formed by the housing 2. The contact surface 32 faces in the proximal direction, wherein the stop surface 21 faces in the distal direction. The barring means 31 has a cam 33 that protrudes towards the longitudinal axis L. The cam 33 is arranged between the free end and the spring-mounted section of the barring means 31. The triggering member 3 has a sleeve-like section 34, wherein a first slot 35 is formed between said sleeve-like section and the barring means 31. The housing 2 has a sleeve-like section 24, wherein a second slot 23 is formed between the sleeve-like section 24 and the stop 21, in particular a housing section 22, which forms the stop 21.

The triggering member 3 is shiftable relative to the housing 2 in the proximal direction, wherein the sleeve-like section 34 of the triggering member 3 is or can be shifted into the second slot 23, and the stop 21, in particular the housing section 22, is or can be shifted into the first slot 35.

By shifting the triggering member 3 in distal direction to the point that it is in a triggering position, the product dispensing or a puncturing procedure can be triggered in a known manner.

Figure 1A:
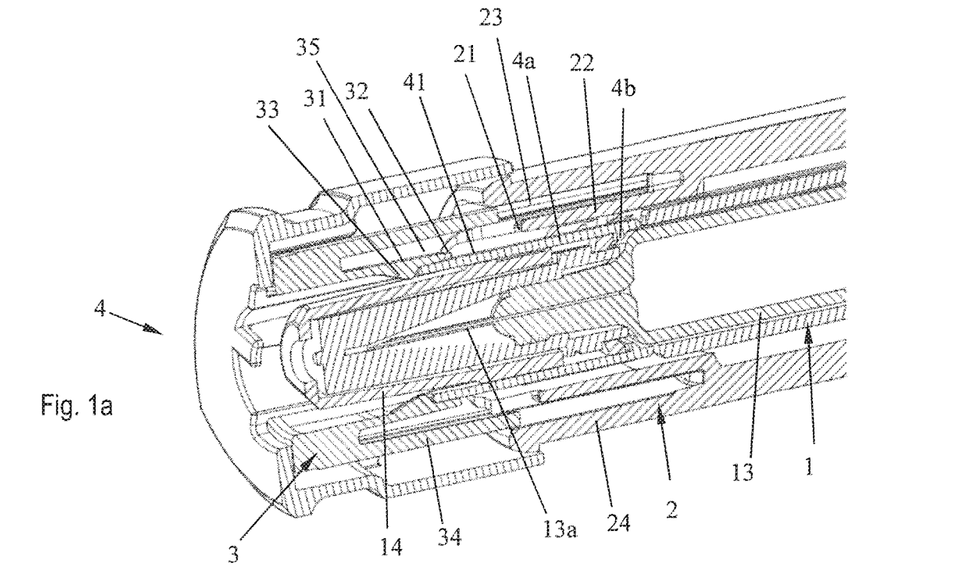
FIGS. 1a and 1b are different cross-sectional representations of a distal section of an autoinjector with covering cap arranged on the housing.
Figure 1B:
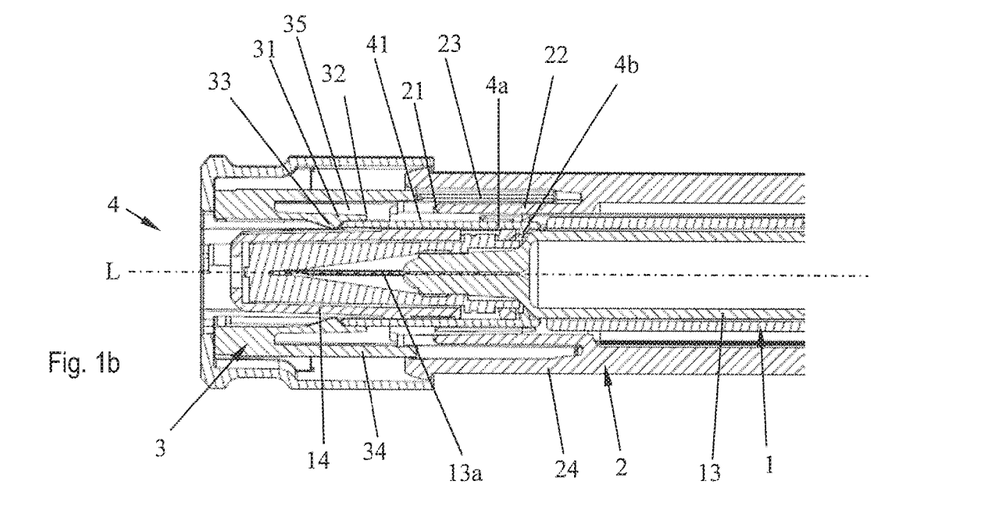

In FIGS. 1a and 1b, the covering cap 4 is in its position attached to the housing 2. The covering cap 4 forms a retention surface 41, which is arranged proximally relative to the cam 33 when the triggering member 3 is in its starting position (FIGS. 1a and 1b). Distally relative to the retention surface 41, the covering cap 4 has a recess for the cam 33, so that, due to its spring-mounted arrangement, the barring means 31 is in a release position or in a position outside of its barring position, wherein the cam 33 is arranged in this recess. The contact surface 32 is here outside of an axial alignment along the longitudinal axis L with the stop 21.

For example, if the autoinjector is accidentally dropped on the floor, then, under some circumstances, the triggering member 3 can be shifted due to its inertia relative to the housing 2 in the proximal direction. In order to prevent the triggering member 3 from being shifted in the process to the point that it is in its release position, which would result in an unintentional triggering of the product dispensing, the movement of the triggering member 3 into its release position is prevented due to the barring means 31, particularly the contact surface 32, abutting against the stop 21 of the housing 2.

Figure 2A:
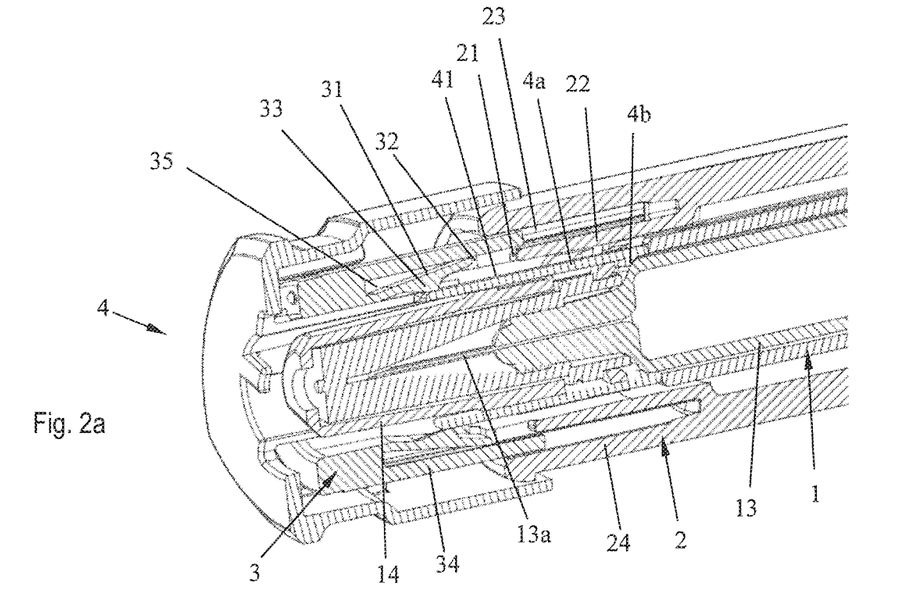
FIGS. 2a and 2b are the views from FIGS. 1a and 1b, wherein a barring means is in its barring position.
Figure 2B:
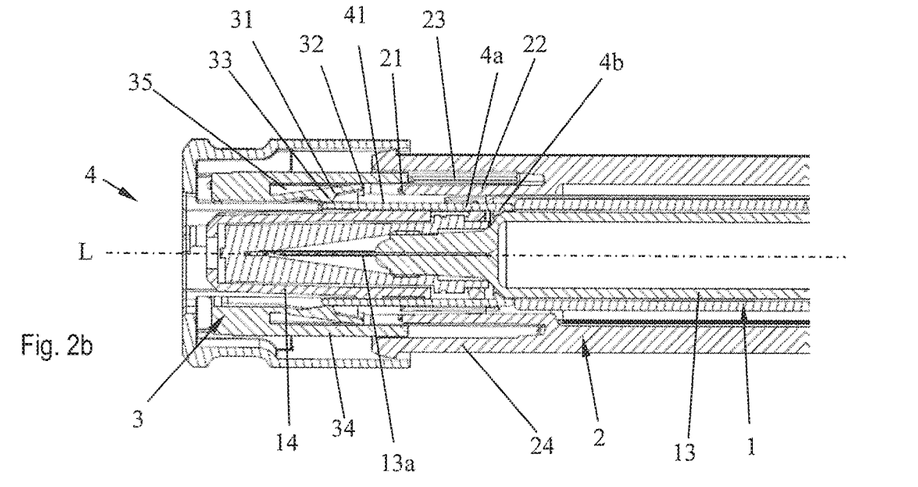

If, with covering cap 4 mounted, the triggering member 3 is moved from its starting position (FIGS. 1a and 1b) relative to the housing 2 in the proximal direction, the barring means 31 is deflected from its release position (FIGS. 1a and 1b) into the barring position (FIGS. 2a and 2b). For this purpose, the covering cap 4 has an actuator or drive surface, on which the cam 33, in particular a beveled drive surface of the cam 33, slides. As a result, the cam 33, and thus also the barring means 31, is resiliently deflected, in particular away from the longitudinal axis L. The retention surface 41 which faces away from the longitudinal axis L, i.e., which faces outward, against which the cam 33 then abuts, retains the barring means 31 in its barring position (FIGS. 2a and 2b). In the barring position, the contact surface 32 is in axial alignment along the longitudinal axis L with the stop 21. The effect of this is that the contact surface 32 abuts against the stop 21, and thus a movement of the triggering member 3 to the point that it is in its release position is blocked. This advantageously has the effect that an unintentional triggering of the autoinjector is prevented as long as the covering cap 4 is attached to the housing 2.

For the preparation of the dispensing of the product, the covering cap 4 is removed from the housing 2. As a result of the removal of the covering cap 4, a needle covering cap 14 that covers the needle 13a is removed from the product container 13 at the same time. In the starting or delivery state of the autoinjector (e.g., FIGS. 1a and 1b), i.e., when the covering cap 4 is arranged on the autoinjector, the needle 13a is covered by the needle covering cap 14, which, in the examples shown, is designed as a so-called "rigid needle shield," alternatively also as a "soft needle shield," which are the terms by which they are known to the person skilled in the art, in order to protect the needle 13a against soiling or maintain the sterility of the needle 13a and of the medication. The needle covering cap 14 is arranged on a needle holding section of the syringe body, wherein the tapering section of the syringe body is located between the needle holding section and the cylindrical section of the syringe body. The shoulder of the syringe holder is arranged between the syringe body and the proximal end of the needle covering cap 14, in particular in such a manner that an albeit also smaller slot forms between the needle covering cap 14 and the shoulder, in order to prevent the shoulder from exerting a force on the needle covering cap 14, which could jeopardize, for example, the sterility of the needle 13a or of the liquid product. The covering cap 4 is detachably snapped on the housing 2 or on a needle guard sleeve 3, wherein this snap-in connection is undone when the covering cap 4 is removed from the housing 2 or from the needle guard sleeve 3. The snap-in connection can be formed, for example, by means of a snap-in geometry. The covering cap 4 comprises, in particular, a snap-in hook 4a, which comprises a catch 4b, which engages in a gap between the needle body, in particular the tapering region thereof, and the proximal end of the needle covering cap 14. When the covering cap 4 is removed from the autoinjector, the catch 4b hooks into the proximal end of the needle covering cap 14, as a result of which the needle covering cap 14 is detached from the product container 13 and removed together with the covering cap 4 from the autoinjector (FIGS. 3a and 3b).

Figure 3A:
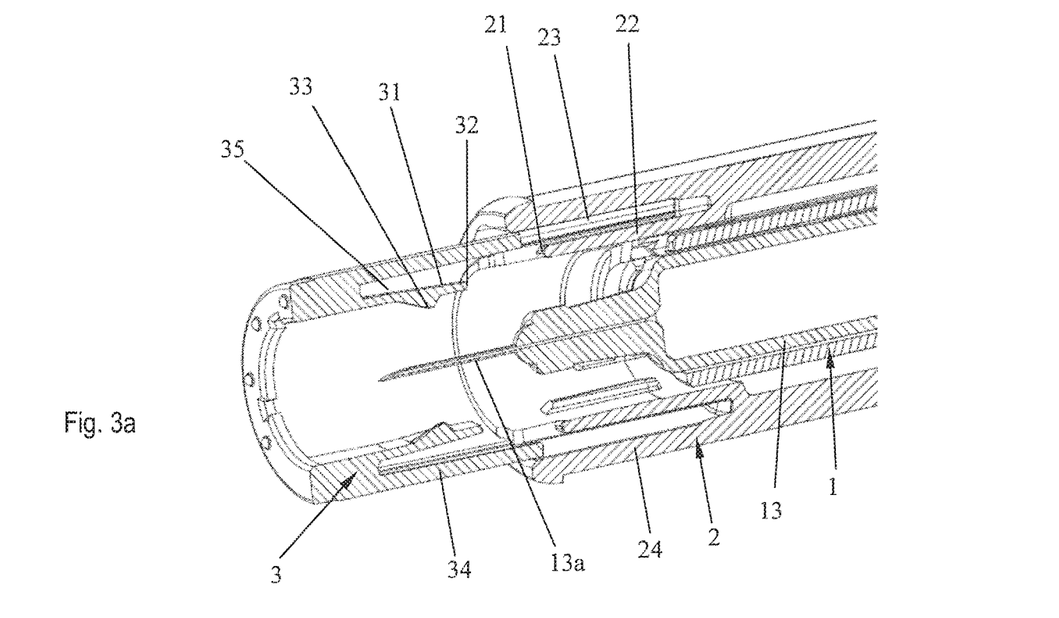
FIGS. 3a and 3b are the views from FIGS. 1a and 1b, wherein the covering cap is removed.
Figure 3B:
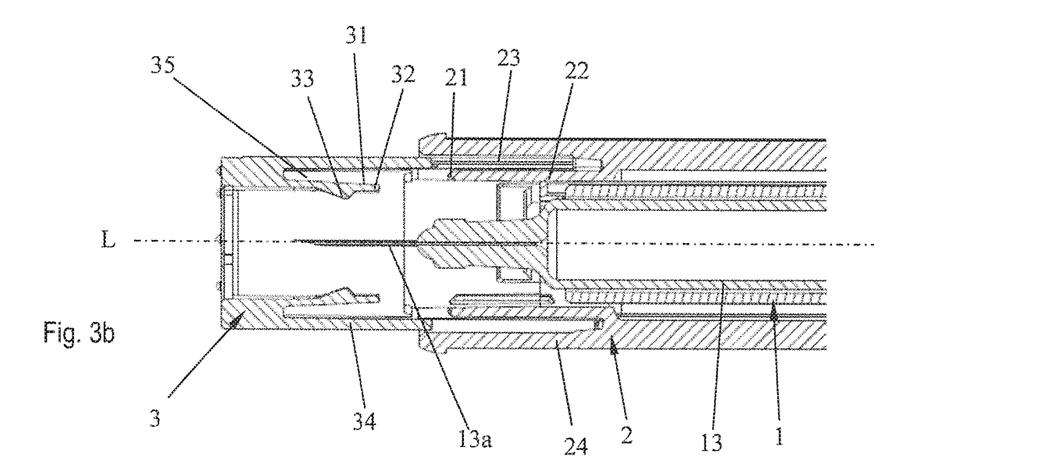

In FIGS. 3a and 3b, the front portion of the autoinjector is represented, wherein the covering cap 4 is removed together with the needle covering cap 14. The autoinjector is thereby prepared for the dispensing. For the dispensing, the distal end of the triggering member 3 is set on the desired puncture site of the patient. The housing 2 is pushed by the user towards the puncture site, wherein, as a result, the triggering member 3 moves relative to the housing 2 in the proximal direction. Due to the covering cap 4 being removed, the barring means 31 is no longer deflected into the barring position. The barring means 31 is in its release position. The triggering member 3 can thus be shifted into its triggering position (FIGS. 4a and 4b), wherein the contact surface 32 is moved past the stop 21, since the contact surface 32 is not in an axial alignment along the longitudinal axis L with the stop 21.

Figure 4A:
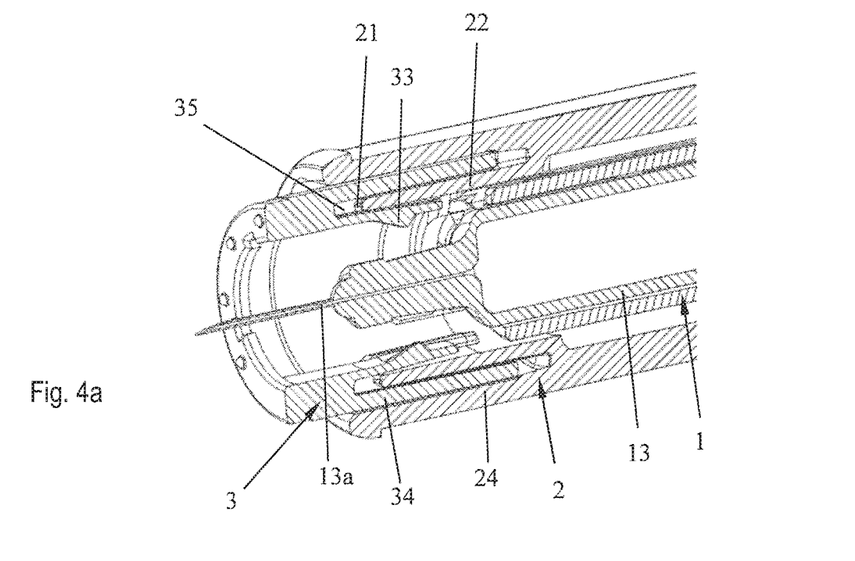
FIGS. 4a and 4b are the views from FIGS. 3a and 3b, wherein a triggering member is in its triggering position.
Figure 4B:
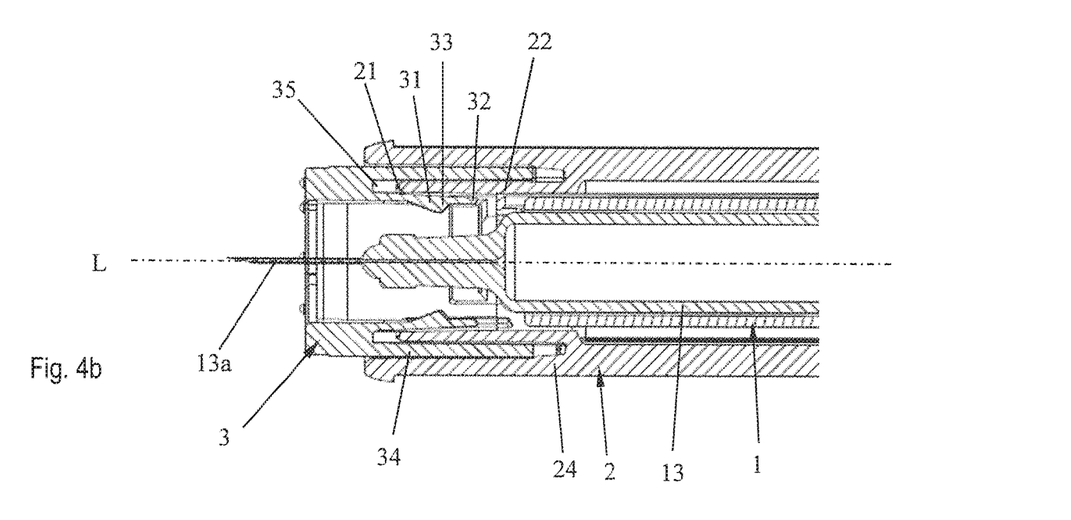

In the triggering position shown in FIGS. 4a and 4b, the injection needle 13a protrudes beyond the distal end of the triggering member 3, in particular by a distance corresponding to the desired depth of insertion. In the starting position (FIGS. 3a and 3b), the injection needle 13a is enclosed by the preferably sleeve-like triggering member 3. In particular, the triggering member 3 protrudes distally beyond the distal end of the injection needle 13a when the triggering member is in its starting position.

After the product dispensing has occurred, it is possible, for example, by the movement of the triggering member 3 in the proximal direction, for a tensioned spring to shift the triggering member 3 relative to the housing 2 in the distal direction, in order to assume a needle guarding position (not shown), in which the distal end of the triggering member 3 protrudes beyond the distal end of the injection needle 13a. In the needle guarding position, the triggering member 3 is preferably engaged with the housing 2 in such a manner so that it can no longer be shifted in the proximal direction, or at least it can no longer be shifted to the point that the distal end of the injection needle 13a protrudes from the distal end of the needle guard sleeve 3.

What is claimed is:

1. An autoinjector for dispensing a liquid product, comprising:
    a housing;
    a product container configured to hold the liquid product and arranged in the housing, the product container comprising a piston shiftable in a distal direction by a drive member for product dispensing;
    a covering cap removably arranged on a distal end of the housing; and
    a triggering member configured to protrude beyond the distal end of the housing in a starting position, the triggering member comprising barring means spring-mounted thereon, and the barring means comprising a contact surface,
    wherein:
    when the covering cap is removed from the housing, the triggering member is movable in a proximal direction relative to the housing from the starting position into a triggering position for triggering product dispensing by way of the barring means being in a release position such that the barring means can be moved past a stop formed by the autoinjector, and
    when the covering cap is arranged on the distal end of the housing, the triggering member is blocked against moving into the triggering position by way of the barring means deflectable by the covering cap into a barring position in which the barring means faces the stop such that the contact surface of the barring means abuts against the stop when the triggering member is moved from the starting position in the proximal direction.

2. The autoinjector of claim 1,
    wherein the barring means assume the release position when the covering cap has been removed such that the barring means can be moved past the stop.

3. The autoinjector of claim 1, wherein the housing comprises the stop.

4. The autoinjector of claim 1, wherein the barring means is spaced apart from the stop along a longitudinal axis of the housing when the triggering member is in the starting position.

5. The autoinjector of claim 1, wherein the covering cap comprises a retention surface, wherein the barring means is retained by the retention surface when in the barring position.

6. The autoinjector of claim 5, wherein the retention surface is configured such that the barring means, which can be moved together with the triggering member, is retained by the retention surface when the barring means has been moved towards the stop and the triggering member has been moved from the starting position in the proximal direction.

7. The autoinjector of claim 5, wherein the covering cap deflects the barring means into the barring position when the triggering member is moved from the starting position in the proximal direction.

8. The autoinjector of claim 5, wherein the barring means comprises a cam configured to be retained by the retention surface and/or slide on the covering cap such that the cam and the barring means are deflected by the covering cap.

9. The autoinjector of claim 1, wherein the contact surface faces in the proximal direction.

10. The autoinjector of claim 1, the triggering member further comprising a sleeve-like section such that the triggering member defines a first slot between the sleeve-like section and the barring means,
    the housing further comprising a sleeve-like section such that the housing defines a second slot between the sleeve-like section of the housing and the stop,
    the sleeve-like section of the triggering member being movable into the second slot and/or the stop being movable into the first slot when the triggering member is moved into the triggering position.

11. The autoinjector of claim 1, further comprising a spring, the spring being tensioned when the triggering member is moved from the starting position in the proximal direction, and the triggering member being shiftable in the distal direction by means of the spring.

12. The autoinjector of claim 1, the product container further comprising a needle, and the triggering member protruding distally beyond a distal end of the needle when the triggering member is in the starting position and/or when product dispensing occurs.

13. The autoinjector of claim 1, the product container further comprising a needle, the needle covered by a needle covering cap removably coupled to the product container, and the covering cap being coupled to the needle covering cap such that when the covering cap is removed from the housing, the needle covering cap is removed from the product container.

14. The autoinjector of claim 1, further comprising a drive spring configured to act on a drive member, the drive spring pre-tensioned such that it can dispense the product from the product container by shifting the drive member by a dispensing stroke, thereby shifting the piston.

15. A safety mechanism for an autoinjector for dispensing a liquid product, the safety mechanism comprising:
    a covering cap and a triggering member, the covering cap being removably arranged on a distal end of a triggering member, the triggering member being adapted to protrude beyond a distal end of the autoinjector and be movable in a proximal direction of the autoinjector from a starting position into a triggering position for triggering product dispensing, the triggering member comprising barring means, and the barring means comprising a contact surface;
    wherein:
    when the covering cap is removed from the triggering member, the triggering member along with its barring means is adapted to be movable from the starting position into the triggering position, and
    when the covering cap is arranged on the distal end of the triggering member, the triggering member is blocked against moving into the triggering position by way of the barring means deflectable by the covering cap into a barring position in which the barring means faces a stop formed by the autoinjector such that the contact surface of the barring means abuts against the stop when the triggering member is moved from the starting position in the proximal direction.

16. The safety mechanism of claim 15, wherein the barring means are spring-mounted and assume a release position when the covering cap has been removed such that the barring means can be moved into the triggering position.

17. The safety mechanism of claim 16, wherein the covering cap comprises a retention surface, wherein the barring means is retained by the retention surface when in the barring position.

18. The safety mechanism of claim 17, wherein the retention surface deflects the barring means into the barring position when the triggering member is moved from the starting position in the proximal direction.

19. The autoinjector of claim 1, wherein the barring means are elongate and extend approximately parallel to a longitudinal axis of the housing, with a free end facing in the proximal direction.

* * * * *